US006910393B2

(12) United States Patent
Muzzio et al.

(10) Patent No.: US 6,910,393 B2
(45) Date of Patent: Jun. 28, 2005

(54) POWDER SAMPLING METHOD AND APPARATUS

(75) Inventors: Fernando J. Muzzio, Monroe Township, NJ (US); Albert Alexander, Somerset, NJ (US); Dean Brone, Pomona, NY (US); Michael Roddy, Cincinnati, OH (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/148,979

(22) PCT Filed: Dec. 11, 2000

(86) PCT No.: PCT/US00/33529

§ 371 (c)(1),
(2), (4) Date: Oct. 10, 2002

(87) PCT Pub. No.: WO01/42760

PCT Pub. Date: Jun. 14, 2001

(65) Prior Publication Data

US 2003/0221495 A1 Dec. 4, 2003

Related U.S. Application Data

(60) Provisional application No. 60/169,929, filed on Dec. 10, 1999.

(51) Int. Cl.[7] ............................................. G01N 1/00
(52) U.S. Cl. ..................... 73/863; 73/864.4; 73/863.82
(58) Field of Search .......................... 73/863, 864.44, 73/863.71, 863.82, 864.63

(56) References Cited

U.S. PATENT DOCUMENTS

| 1,109,446 | A |   | 9/1914  | Melberg |
| 3,604,269 | A |   | 9/1971  | Smith et al. ................... 73/422 |
| 4,172,385 | A | * | 10/1979 | Cristensen ............... 73/864.63 |
| 4,685,339 | A |   | 8/1987  | Philipenko ............... 73/864.45 |
| 5,470,535 | A |   | 11/1995 | Ray et al. .................... 422/101 |
| 5,476,017 | A | * | 12/1995 | Pinto et al. .............. 73/864.62 |
| 5,703,301 | A |   | 12/1997 | Pinto et al. .............. 73/864.63 |
| 5,996,426 | A |   | 12/1999 | Robinson et al. ......... 73/864.63 |
| 6,054,099 | A | * | 4/2000  | Levy .......................... 422/102 |
| 6,171,280 | B1 | * | 1/2001 | Imazu et al. ................ 604/118 |

OTHER PUBLICATIONS

Muzzio, FJ et al., "An Improved Powder–Sampling Tool," Pharmaceutical Technology, pp. 92–109, Apr. 1999.

* cited by examiner

*Primary Examiner*—Hezron Williams
*Assistant Examiner*—Rodney Frank
(74) *Attorney, Agent, or Firm*—Wolff & Samson PC

(57) ABSTRACT

A powder sampling method and apparatus is provided for sampling powder from a mixer or a drum. An undisturbed column of powder is extracted from a vessel. The column of powder may then be sectioned into subunits, using a discharge device, providing up to dozens of samples per insertion. Larger number of representative samples of controlled size from a powder bed can be acquired.

15 Claims, 10 Drawing Sheets

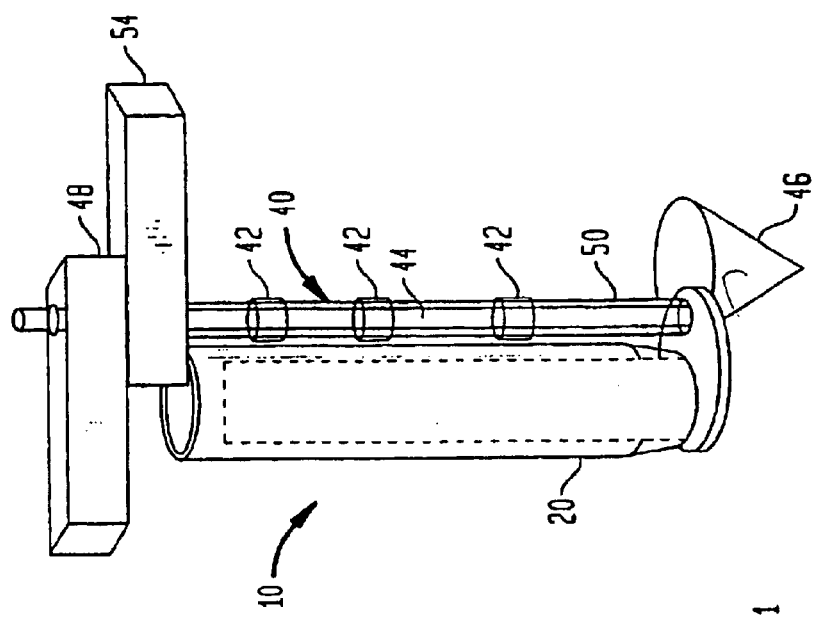
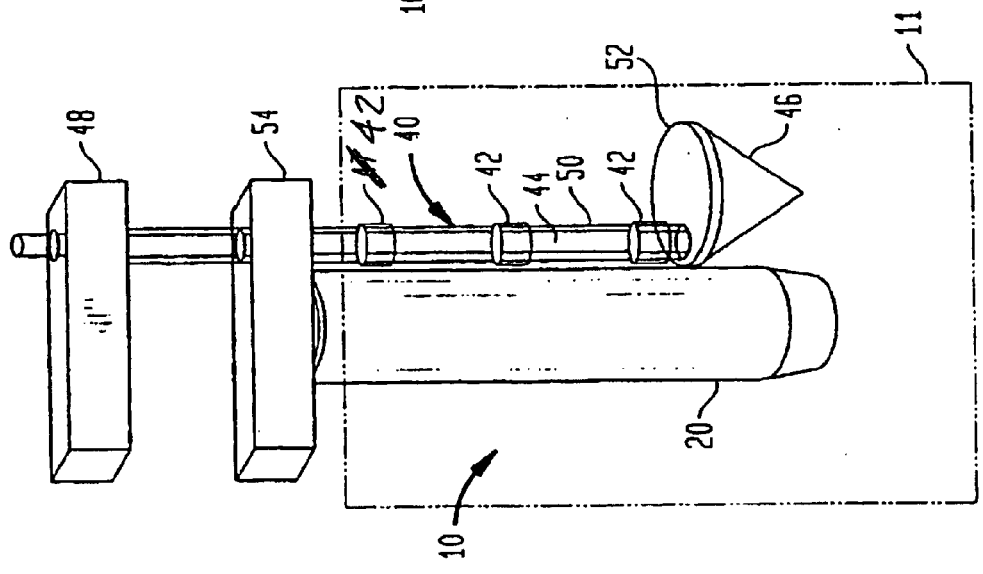
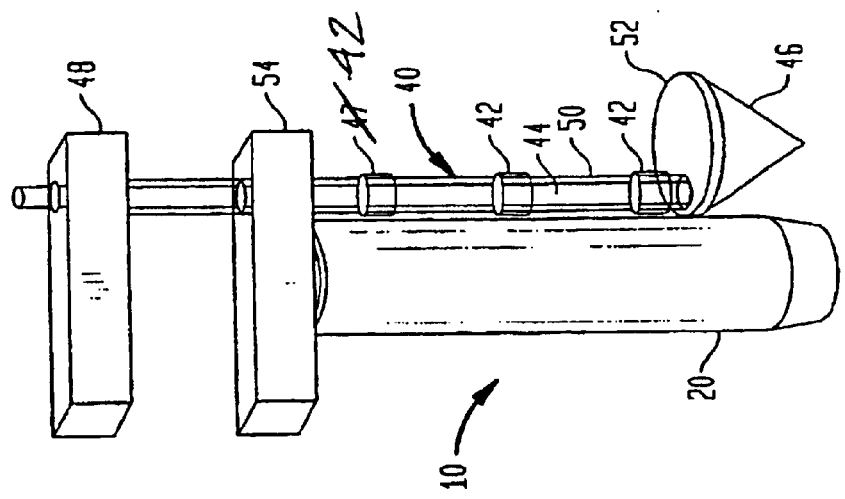

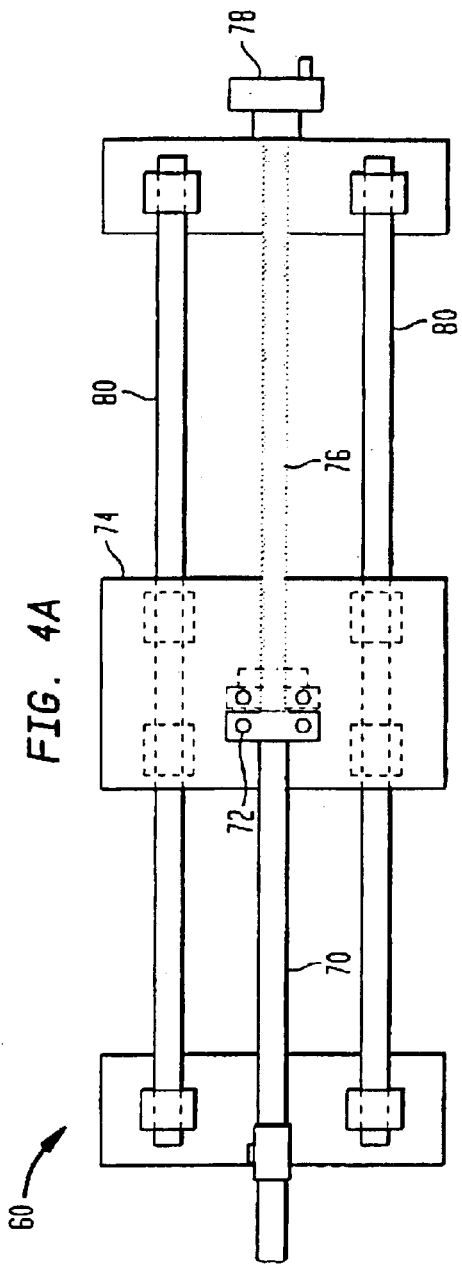
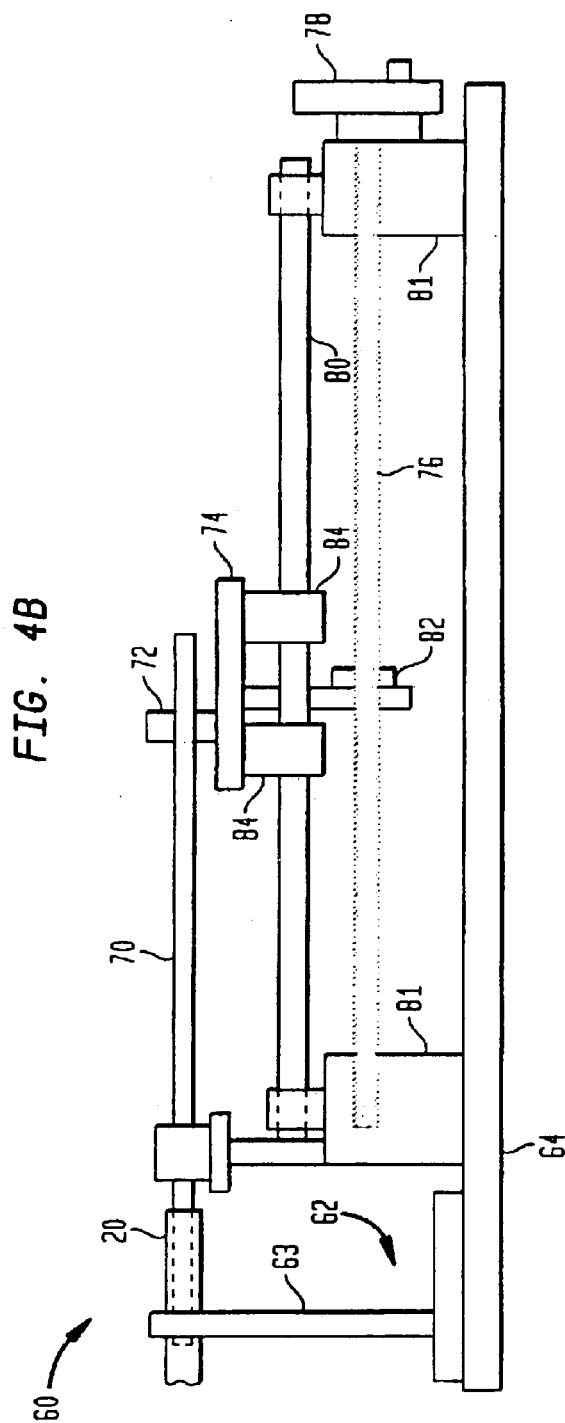
FIG. 4A
FIG. 4B

POWDER SAMPLING METHOD AND APPARATUS

RELATED APPLICATIONS

This is a U.S. National Phase Application under 35 U.S.C. § 371 of PCT Application No. PCT/US00/33529 filed Dec. 11, 2000, which claims the benefit of U.S. Provisional Patent Application Ser. No. 60/169,929 filed Dec. 10, 1999, the entire disclosures of which are expressly incorporated herein by reference.

BACKGROUND OF THE INVENTION

1. Field of the Invention

The present invention generally relates to a method and apparatus for sampling powder, and moves specifically to a method and apparatus for powder sampling which obtains undisturbed powder samples.

2. Related Art

Powdered materials are used in a wide range of industries. For example, an estimated 80% of pharmaceutical products take the form of tablets, which are compacts of powders. Powdered ingredients such as starches, flour, and sugars are essential raw materials in the food industry. Inorganic powders, such as oxides, nitrides, and carbides are used as raw materials in the ceramic industry. Detergents, abrasives, cosmetics, fertilizers, catalysts, etc., also involve processing powdered components.

Achieving homogeneous and well-characterized blends of powders and granules is a critical step in the manufacture of pharmaceutical tablets. Ineffective powder blending can result in increased variability in the contents of potent components in tablets, often resulting in rejection of finished product due to poor quality. If mixing inhomogeneities could be identified and/or avoided during the manufacturing process, fewer batches would be rejected, thus reducing manufacturing costs for existing products and perhaps decreasing time-to-market for new products.

At the present time, blending of granular materials is largely an art rather than a science. The ability to design and accurately assess a mixing process for a high potency drug is limited. Recognition of this problem has recently resulted in lawsuits and in tightening of FDA regulations. The situation is complicated by the lack of effective techniques for characterizing powder mixtures. In fact, the state of the art in sampling procedures (the thief probe) is often so inaccurate that it is possible for a high quality batch to be rejected due entirely to sampling error. Poor sampling capabilities have resulted in a lack of rigorous quantitative evaluations of actual powder mixing processes, further hindering both process development and quality control.

Characterization of homogeneity in a powder system is usually attempted by taking and analyzing discrete samples. The most common approach in stationary powder systems is to use a thief probe to withdraw samples from different locations. Thief samplers belong to two main classes, side-sampling and end-sampling. A typical side-sampling probe has one or more cavities stamped in a hollow cylinder enclosed by an outer rotating sleeve. The sleeve has holes that align with the cavities, allowing adjacent powder to flow into the cavities. An end-sampling thief has a single cavity at the end of the probe; such cavities can be opened and closed in a controlled manner. In both cases, the thief is introduced into the powder with the cavities closed. Once insertion is complete, the cavities are opened, allowing the powder to flow into them. The cavities are then closed, and the thief is withdrawn, removing samples from the mixture.

In principle, the homogeneity of the mixture may be statistically estimated from these samples. However, this estimate is meaningful only if the probe itself does not introduce errors. As mentioned above, this is not always the case. Errors are often introduced both when the theif probe is inserted into the powder bed and when powder flows into the thief cavities. In any sampling scheme, the experimentally measured variance, $\sigma_e^2$, is actually a combination of the true variance resulting from the mixing process, $\sigma_m^2$, the variance introduced by sampling error, $\sigma_s^2$, and the variance resulting from chemical analysis, $\sigma_a^2$. In addition, for granular materials, any sample is composed of a finite number of particles, and there is a residual irreducible variance $\sigma_r^2$ i.e., $$\sigma_e^2 = \sigma_m^2 + \sigma_s^2 + \sigma_a^2 + \sigma_r^2 \qquad (1)$$

In an ideal situation, $\sigma_s^2$, $\sigma_a^2$ and $\sigma_r^2$ are negligible, and $\sigma_e^2$ (the variance subject to USP rules) is almost identical to $\sigma_m^2$ (the true variance). Unfortunately, thief probes often bias measurements to the point that sampling uncertainty is a large fraction of the measurement. Thief probes often introduce two types of errors: (i) the mixture is extensively disturbed when the thief probe is inserted into the powder bed, and (ii) particles of different size flow unevenly into the thief cavities. As a result of such errors, a homogeneous mixture can be deemed inadequate due entirely to sampling error.

Accordingly, what is needed, but has not heretofore been provided, is a powder sampling tool that preserves the homogeneity of the mixture and minimizes disturbance of the powder bed.

OBJECTS AND SUMMARY OF THE INVENTION

It is an object of the present invention to provide a thief probe system to render undisturbed samples in far more accurate and convenient manner than conventional thief probes.

It is another object of the present invention to provide a thief probe system that minimizes disturbance of a powder bed while obtaining samples.

It is an additional object of the present invention to provide a powder sampling method and apparatus which utilizes a cylindrical tube with a sharp or pointed circular lower edge for obtaining samples while minimizing disturbance of the powder.

It is a further object of the present invention to provide a powder sampling method and apparatus includes a cap for retaining powder within the sampler during retraction of the sampler from powder.

It is a further object of the present invention to provide a powder sampling method and apparatus which includes a mechanism for removing powder samples from the sampler.

The powder sampler of the present invention comprises a cylindrical tube with a lower end wherein the walls of the cylindrical tube taper to a sharp circular edge. The tube can be inserted into a powder bed to capture a powder sample within the tube. The sample remains within the tube based on arching, or alternatively, a cap can be used to retain the powder in the tube. The sample can then be removed from the tube in increments for testing. A powder extraction apparatus for removing the powder from the tube is included. The extraction apparatus comprises a push rod interconnected with threaded rod such that rotation of the threaded rod pushes the push rod through the cylindrical tube to push out the powder sample.

BRIEF DESCRIPTION OF THE FIGURES

Other important objects and features of the invention will be apparent from the following Detailed Description of the Invention taken in connection with the accompanying drawings in which:

FIGS. 3A, 3B and 3C show an embodiment of the apparatus of FIG. 1 with a capping fixture.

FIG. 4A is a top plan view and FIG. 4B is a side plan view of a core discharge fixture for removing a powder sample from the powder sampling apparatus.

DETAILED DESCRIPTION OF THE INVENTION

Figure 1:
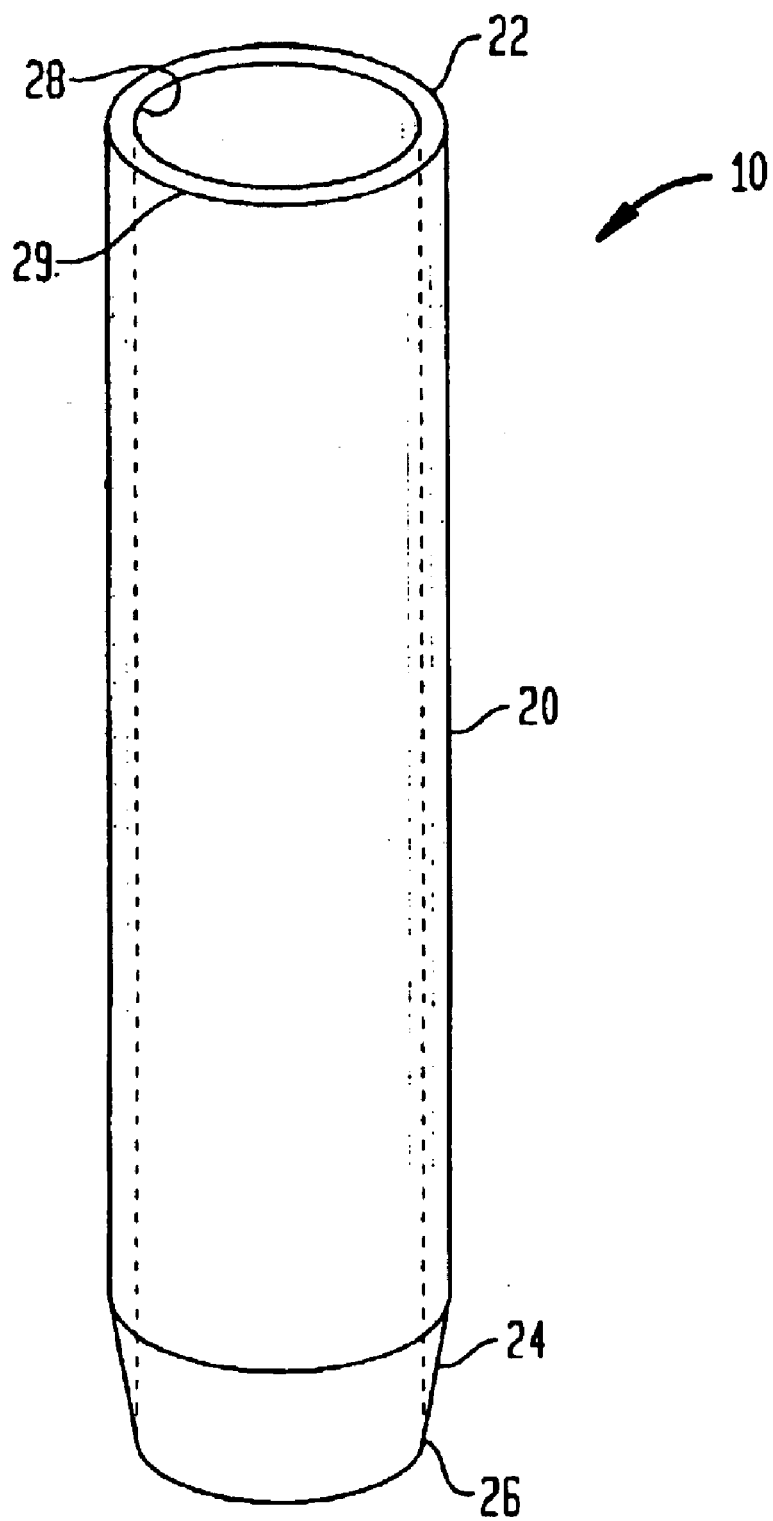
FIG. 1 is a perspective view of the powder sampling apparatus of the present invention.
Figure 2:
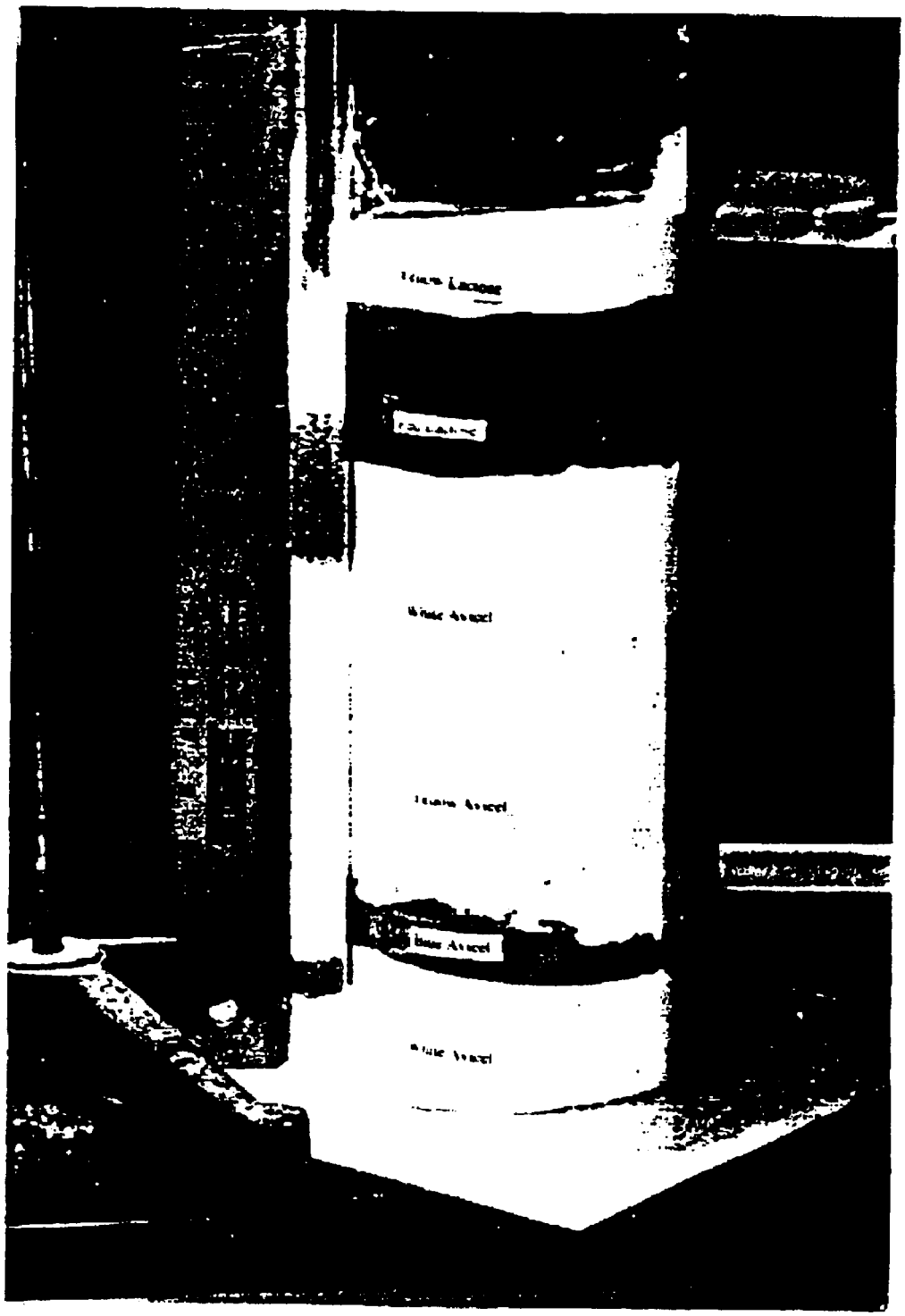
FIG. 2 is shows the powder sampling apparatus of FIG. 1 inserted into a powder.

The present invention relates to a system for sampling powder from a vessel. The device may be herein referred to as a "core sampler." As depicted in FIG. 1, the core sampler of the present invention, generally indicated at 10, comprises a cylindrical tube 20, having an upper end 22 and a tapered lower end 24 which is tapered to a sharp angle 26. The cylinder 20 has an inner wall 28 and an outer wall 29. At the sharp angle 26, the inner and outer walls 28 and 29 meet. The core sampler 10 could be constructed from stainless steel, but other strong metals or polymers would be equally suitable. To gather a sample, the core sampler 10 is inserted into a powder bed to a predetermined depth, thus isolating a cylindrical core of powder within the tube 20. As shown in FIG. 2, by using this approach, a nearly undisturbed column of powder is isolated inside the core sampler 10.

Most materials of interest in pharmaceutical applications are sufficiently cohesive so that they do not drain out of the core sampler 10 under gravity. A simple cylindrical tube 20 is all that is required to pull a column of such powder from the bed. Cohesive powders resist flow due to gravity; they stick within the cylindrical tube 20 due to particle-particle and particle-wall frictional forces which lead to "arching." Since the frictional forces of cohesive powders are high, cohesive powders are prone to arch. Arching will occur more readily in smaller diameter tubes, since the arching distance is decreased, and the ratio of tube surface area to volume of powder within the tube diameter is increased. Therefore, to increase the likelihood of extracting a sample of powder, smaller diameter core samplers may be used. Importantly, the core sampler of the present invention can be used to take vertical samples, samples at an angle, or even horizontal samples. Also, it should be noted that the inner diameter of the core sample can be varied in accordance with the powder being sampled and the size of the sample desired.

However, if smaller diameter cores are not practical, or for extremely free flowing powders, the core can be used with a capping fixture, as shown in FIGS. 3A, 3B and 3C. In this configuration, a fixture 40 designed to cap the end is attached to the exterior of the tube 20 by means of eyelets 42. This capping fixture 40 has two components, (i) a plow rod 44 with a sharp conical plow 46 affixed at one end and a removable plow handle 48 on the opposite end, and (ii) a cap tube 50 with a thin circular disk or cap 52 affixed at one end and a removable cap handle 54 on the opposite end. The practice of using the core sampler 10 comprises of three steps. The starting configuration is depicted in FIG. 3A. The cap tube 50 is slid through the eyelets 42 on the tube 20 and the cap handle 54 is attached at a marked position. The plow rod 44 is then slid within the cap tube 50 and the plow handle 48 is attached. In the starting position, the cap 52 rests flush on top of the plow 46. In step 2, the core sampler 10 is inserted into a powder bed, generally indicated at 11 to a predetermined depth, as shown in FIG. 3B, thus isolating a cylindrical core of powder within the tube 20. In step 3, the open end of the core tube 20 is capped so that the powder core remains in the tube 20 during extraction of the sampler from the powder bed 11. To accomplish this, the plow rod 44 and cap tube 50 are further extended into the powder bed 11 to a level where the cap 52 is just below the level of the core tube 20. The cap tube 50 is then rotated so that the cap 52 covers the end of the core tube 20. Once the sampler is capped, it is pulled from the powder bed, as shown in FIG. 3C. Importantly, the plow 46 and cap 52 do not interfere with the sample within the tube 20. Rather, the cap and plow 52 are moved to below the opening of the tube 20 after the sample is already in the tube 20, thereby eliminating disturbance of the sample by the plow 46 and cap 52.

The present invention also includes a reliable and robust method for discharging the core sample. Since it is desirable to subdivide the powder column into a number of undisturbed samples of controlled weight, the discharge fixture must withstand very large forces sometimes required to move cohesive powders through small diameter cores. The core discharge fixture is generally indicated at 60 in FIGS. 4A and 4B. The fixture 60 comprises a tube holder 62 having an upright flange 63 attached to a metal base 64. The upright flange 63 has an aperture slightly larger than the cylindrical tube 20 for receiving and holding the cylindrical tube 20. Locking screws, not shown, may be used to retain the cylindrical tube 20 securely in place during sample extraction. A push rod 70 is inserted into the cylindrical tube 20 to push the powder sample therefrom. The push rod 70 is driven through the cylindrical tube 20 by a ram comprising a sliding platform 74. The push rod 70 is mounted on the platform 74 by mount support 72. The platform 74 is mechanically coupled to a linear motion system comprising a precision-threaded rod 76, a handwheel 78, guide rails 80, and collars 82 and 84. One collar 82 links the sliding platform to the precision-threaded rod 76, while the other collars 84 connect the sliding platform to the guide rails 80. The linear motion system is attached to the base 64, so no relative motion occurs between the cylindrical tube 20 and the linear motion system. The guide rails 80 are interconnected with the base 64 by attachment to pillow blocks 81. When the handwheel 78 is rotated, the precision-threaded rod 76 turns, moving the sliding platform 74 forward, sending the push rod 70 linearly through the cylindrical tube 20. Sample size is controlled by the number of turns on the handwheel 78. In cases where the material is free flowing, the core discharge fixture 60 can be held at angle of inclination greater than the complement of the angle of repose of the powder. This insures that powder is discharged due to the action of the discharge device and not from gravitational flow.

The performance of the core sampler was evaluated using a layered system of microcrystalline cellulose (Avicel, FMC Corporation) and granulated lactose. The lactose was dyed red in order to distinguish it visually from microcrystalline cellulose, which is white. The powders were classified by sieving. The Avicel exhibited a particle size less than 90 microns. The lactose exhibited a particle size ranging from 500 to 710 microns, nominally 600 microns. A layered system of lactose on top of microcrystalline cellulose was formed in a 2000 ml beaker with a diameter of approximately 4 inches. The Avicel layer was 4 inches thick; the lactose layer was 2.5 inches thick.

The performance of three core samplers with different size inner diameters, 7/8 inch, 11/16 inch and 7/16 inch, were evaluated. The core samplers were used in the manner described in the previous section. The volume of the collected sample may be approximated by the inner diameter of the tube multiplied by the distance which the screw ram is driven between collections. By controlling the number of rotations of the screw driven ram, the size of the collected sample and therefore the number of samples collected from each core was varied. Typically the ram was extended between 0.2 inches and 0.4 inches between samples, corresponding to samples weighing between 0.4 grams and 2 grams. Highly uniform sample weight was achieved by monitoring the sample weight during discharge from the core. Sample weight variability was much lower (relative standard deviation=2%) than for the thief probes described above.

Figure 5:
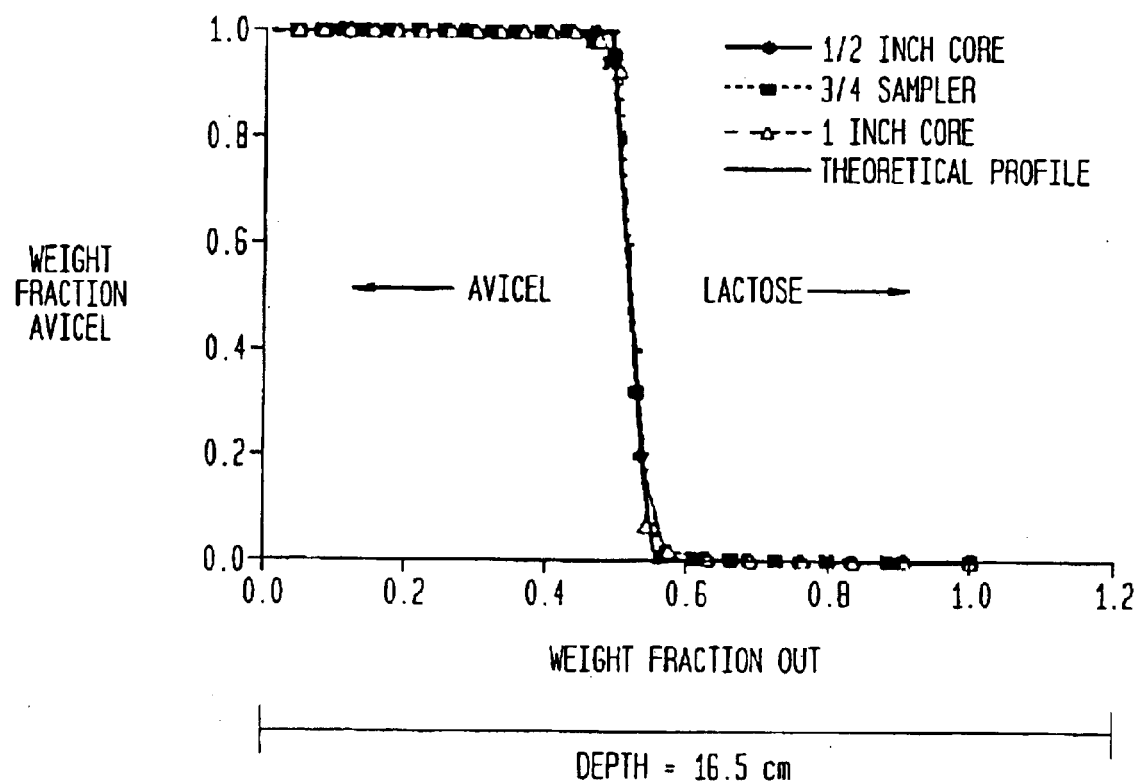
FIG. 5 is a graph of core sample profiles of the interface between Avicel and lactose in a layered system.

FIG. 5 demonstrates the ability of the core sampler to accurately profile the interface between Avicel and lactose in a layered system. In these cases, the extracted core of powder was divided into approximated 20 smaller sections. The composition of the sections was determined by sieve separation (recall the Avicel had a much smaller particle size). The interface between the Avicel and lactose is sharply resolved, with little contamination of Avicel in the lactose layer or vice versa. The axial resolution of the technique was determined to be less than 1 centimeter. That is, the contamination of powder from one stratum to the next is limited to less than 5% after a distance of 1 centimeter. In contrast, other commercial thief probes yield a much smaller number of samples, require similar or larger amount of labor, and exhibit significantly greater contamination.

To describe the uniformity of powder within a large vessel it is often necessary to sample many locations. The core sampler of the present invention is efficient at extracting a column of powder from the vessel, with tight axial resolution, but it is also necessary to take samples at different radial positions. Insertion of the core sampler into the powder bed does disrupt the powder outside of the sampler, especially in cases where the plowing and capping rod are used. It is necessary to take into account the size of the disrupted zone of powder in order to determine the minimum lateral separation between sampling locations required for accurate sampling.

The disrupted zone of powder can be visualized using layered systems. Most of the disruption is caused by the insertion of the plowing and capping rod. On the side of the capping and plowing rods, the disrupted zone of powder extends for up to 5 centimeters from the core. On the side opposite of the capping and plowing rod, the disrupted zone of powder extends less than 1 centimeter from the core. When the capping and plowing rods are used (as would be the case for free flowing powders), a conservative recommendation for the minimum recommended separation between sampling locations is 5 core diameters. When the capping and plowing rods are not used (as in most cases) the minimum separation between sampling locations is 2 core diameters.

Removal of the core sampler causes significant disruption to the powder bed, because powder outside the sampler collapses into the gap left by removal of the core, disrupting powder several centimeters away. Therefore, in order to maintain the highest amount of radial resolution, an adequate strategy for sampling is to insert all of the core samplers into the powder vessel prior to removing any of them. In this manner, the disturbances to the powder bend during removal of the core cannot affect the powder isolated within the other cores.

As an example, core samplers were used to describe the characterization of blend homogeneity in a 2 cubic foot Tote-Blender manufactured by GEI Galley. This device is an asymmetric tumbler with the bottom section shaped as a hopper and the top a rectangular box. The axis of rotation does not bisect the blender into two equal halves but rather a skewed partition in order to break the symmetry of rotation.

Figure 6:
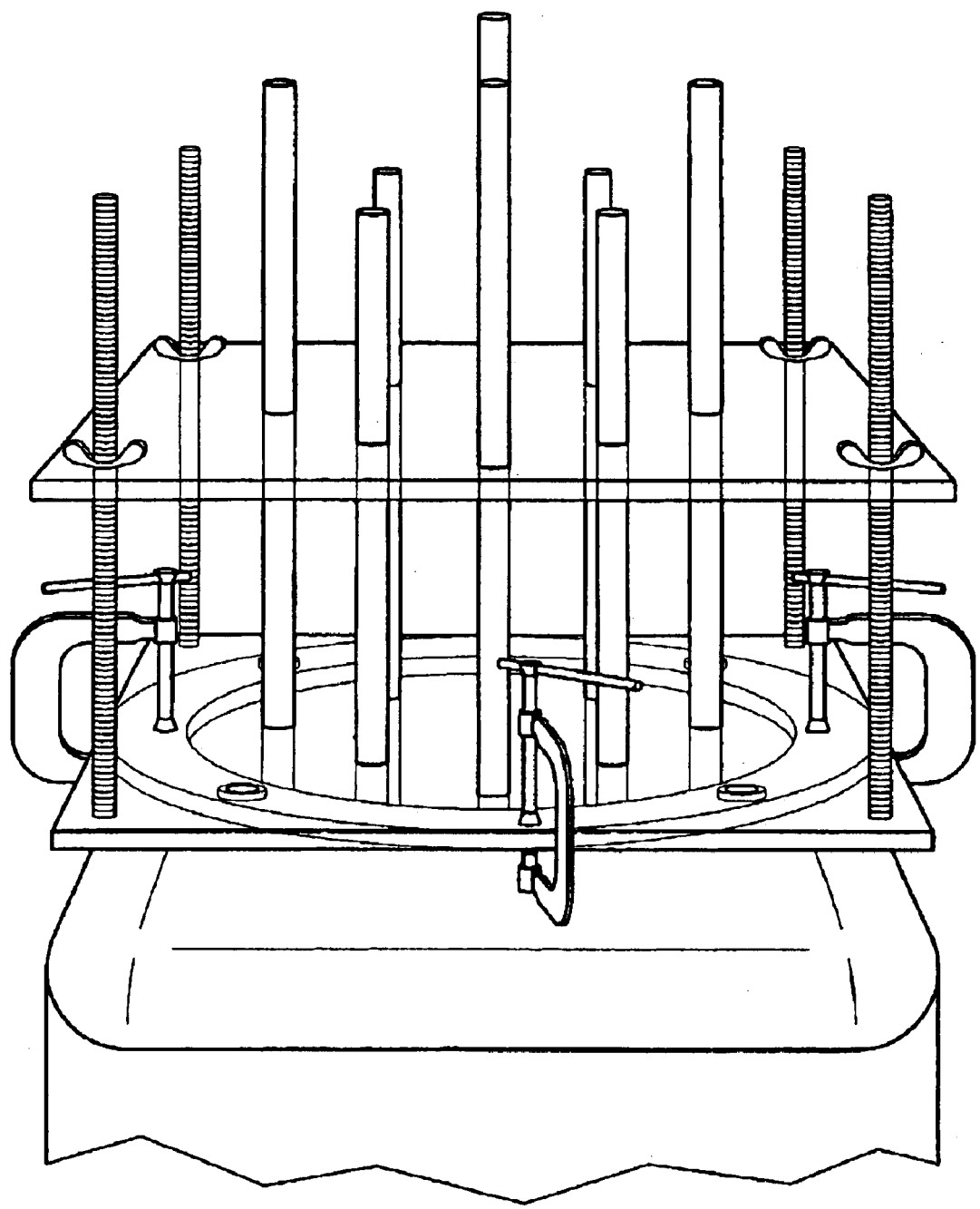
FIG. 6 shows a plurality of sampling tubes extending through a template for taking a plurality of powder samples.
Figure 7:
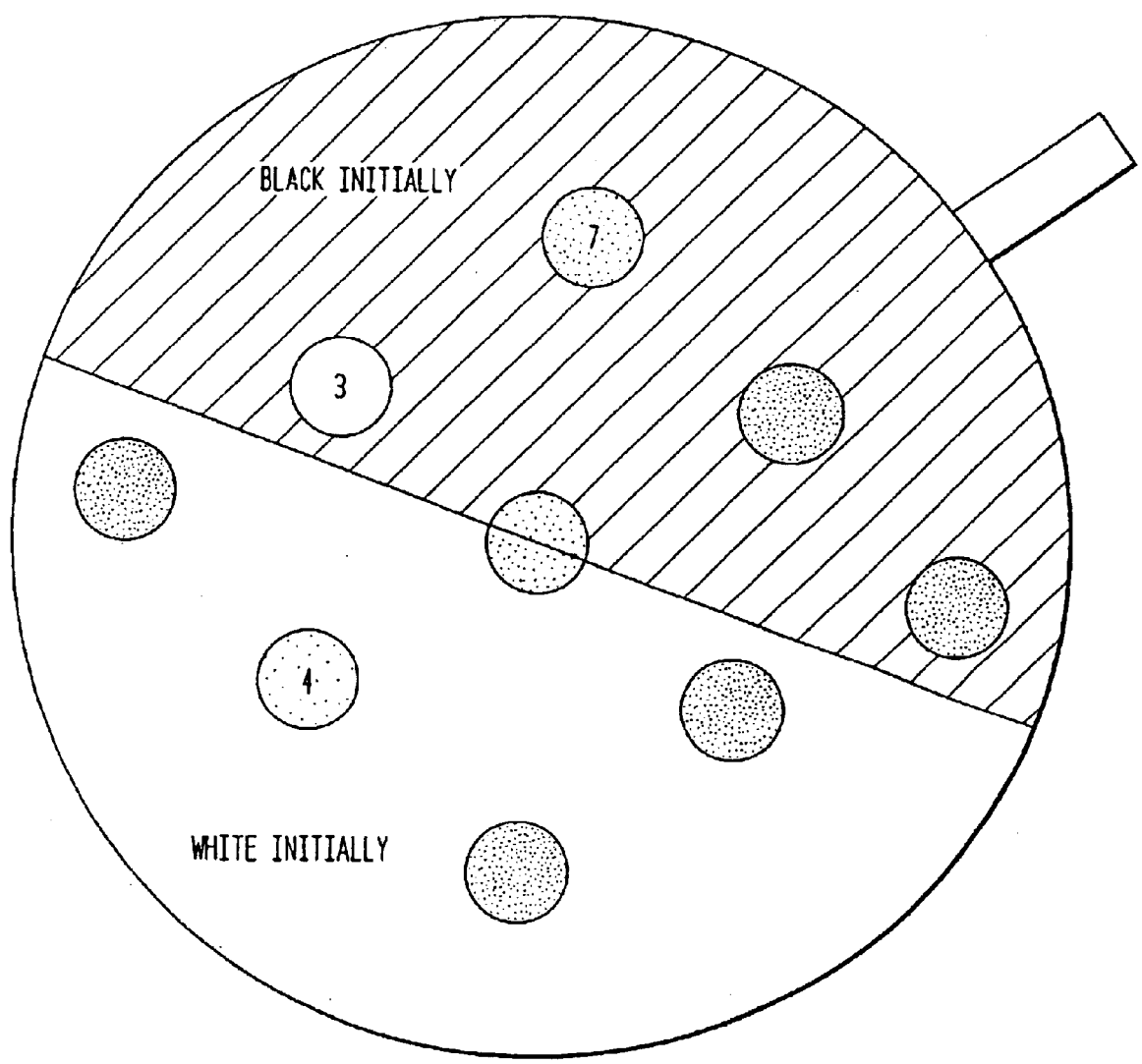
FIG. 7 shows an experimental set-up for taking a plurality of powder samples from a blender.

White and Black Art Sand from Clifford W. Estes Co., Inc., located in Lyndhurst, N.J. was mixed in the tote-blending experiments. The range of particle size was between 0–500 $\mu$m for both colors. Although the sand used in these experiments was free flowing, the core samplers with the capping rod in place did not yield enough samples, necessitating the use of simple cores. A successful sampling strategy was implemented as follows:

(1) At the end of the mixing experiment, the lid of the blender was removed, and a sampling grid, was attached to the top of the blender to maintain consistency in spacing and straight passage through the granular bed as shown in FIGS. 6 and 7.

(2) Core samplers were introduced into the mixture without removing any of them.

(3) Tests in layered system showed that the infiltration process did not disturb the sand within the cores.

(4) The samplers were removed discharged in a controlled manner to subdivide them into multiple samples.

The cores used had an inner diameter of 0.75 inches and the rods were inserted 3.5 inches apart. A total of nine rods spanned the spaced allotted by the opening of the blender.

The sampling procedure and the time spent on each step are provided below for the case of one operator performing the sampling alone.

1. Fix the sampling grid on the tote-blender opening upon completion of a mixing experiment (1 minute).

2. Insert the core samplers into the grid holes making sure the pass through the sand bend until their bottom contact the inner hopper walls (1 minute).

3. Extract each core sampler, take it to the discharge device, and extrudate the sample from each sampler, dividing it into "unit does" samples. This procedure takes 9 minutes.

4. The next step is to process the individual unit-dose samples using an appropriate method of analysis. Time required for this procedure obviously depends on the chemical nature of the material and therefore was not estimated for a general case.

Figure 8:
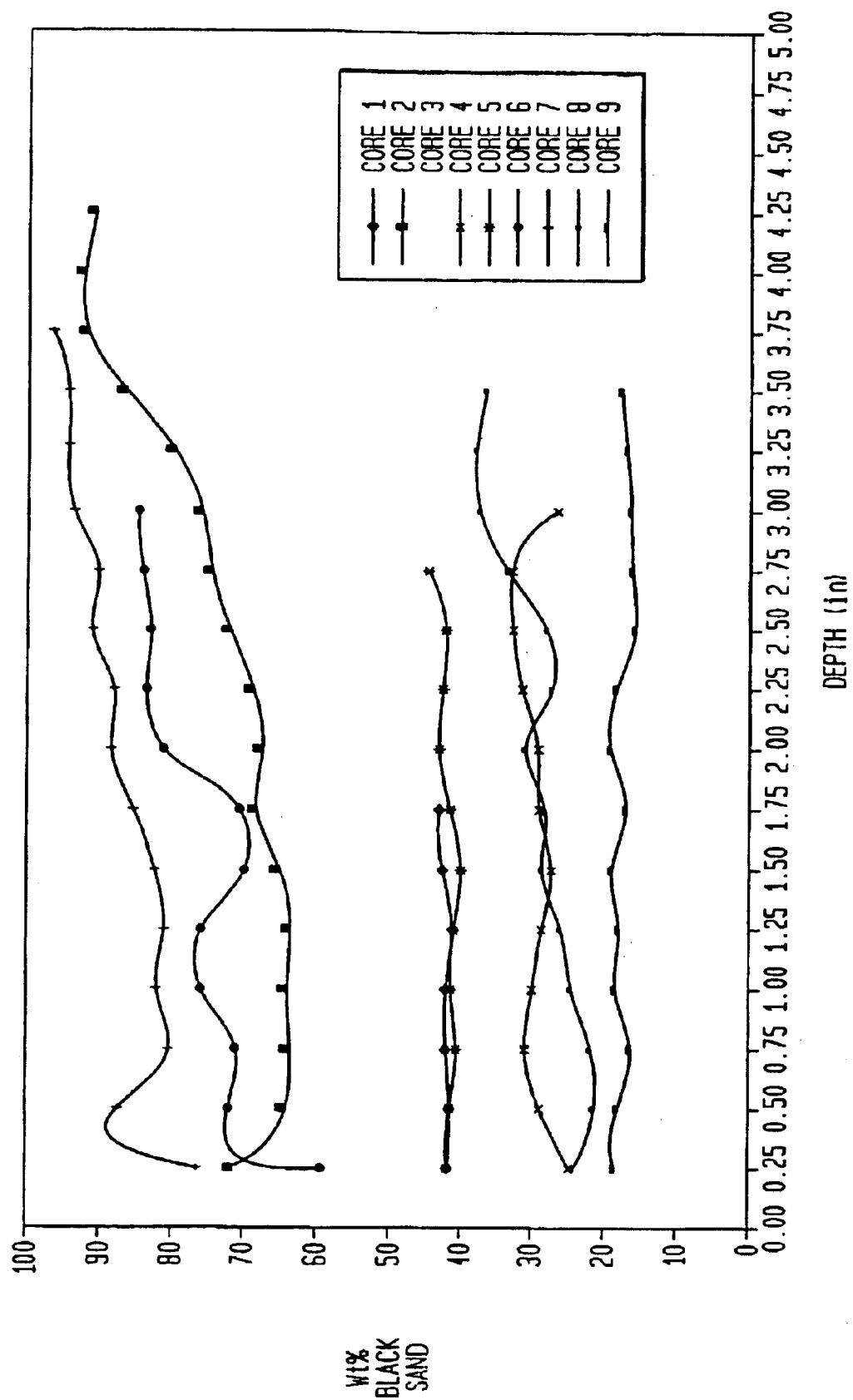
FIG. 8 illustrates the concentration profile for black sand versus depth for each core sampler.
Figure 9:
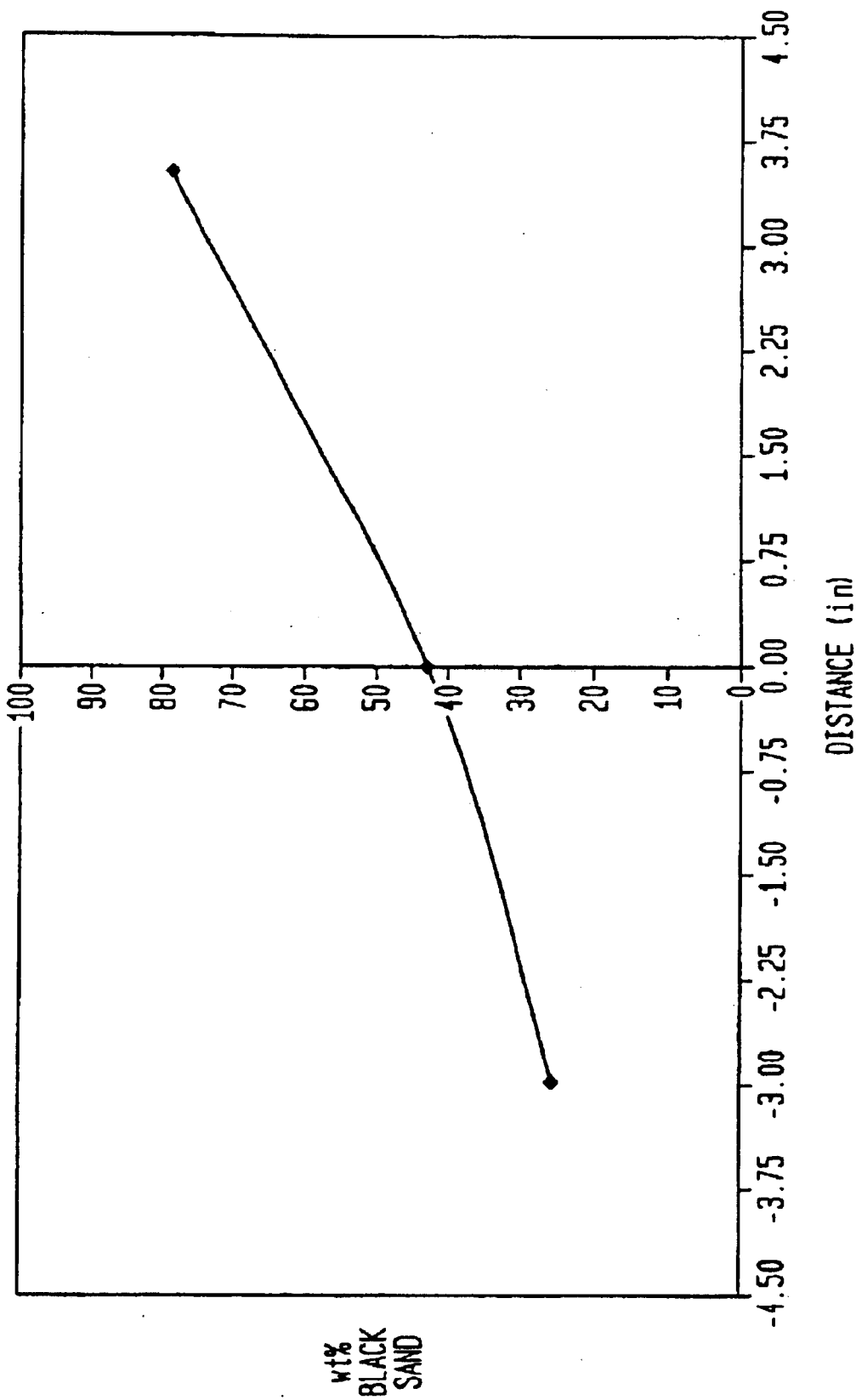
FIG. 9 displays the axial profile after 30 revolutions
Figure 10:
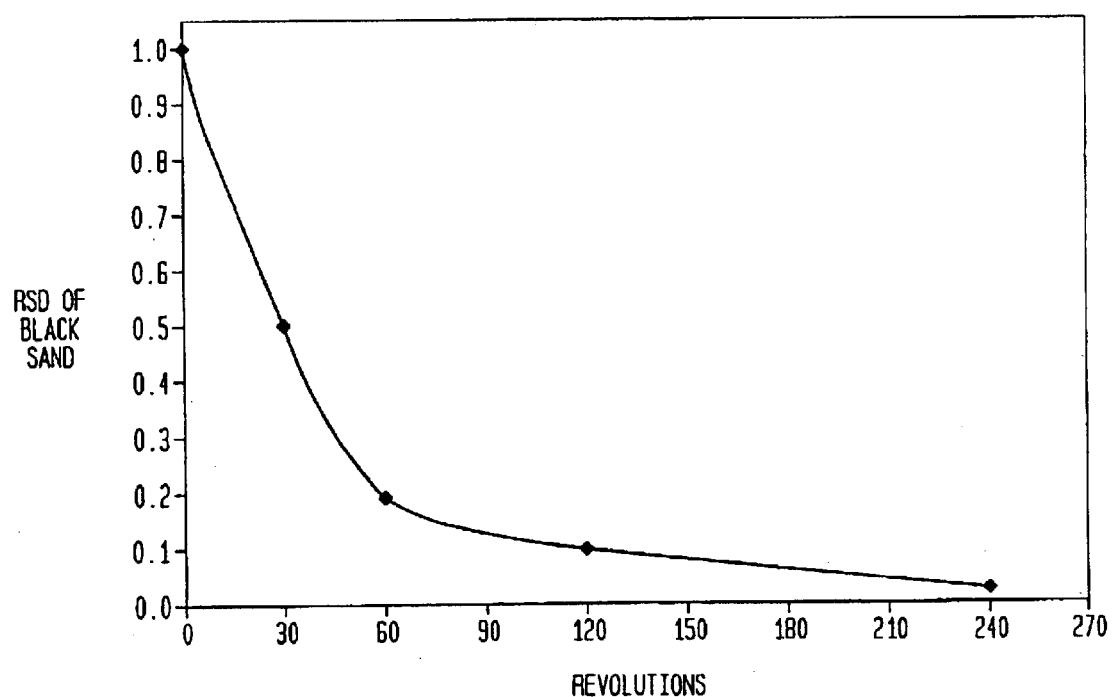
FIG. 10 shows nearly complete homogeneity is achieved after 240 revolutions.

The outcome of this sampling procedure is concentration data. FIG. 8 illustrates the concentration profile for black sand versus depth for each core sampler. The initial condition for this experiment had the black and white sand loaded side by side, each on a different side of the baffle, filling 40% of the total volume of the vessel. FIG. 9 displays the axial profile after 30 revolutions. As it is the case for all tumbling mixers, axial mixing is slow; the regions that had initially one color of sand remained high in concentration of that color for this particular experiment. Cores 7, 2, 6 are placed in the initially black sand region (positive x-axis), while cores 8, 4, 9 are in the initially white region (negative x-axis). Cores 3, 1, 5 approximately sample the division line between the colors as shown in FIG. 7. The entire set of 106 values is reported in Table 1. Mean composition measured by the procedure is 50.44%, in excellent agreement with the amount of black sand initially loaded to the vessel. The RSD is 49%, demonstrating that the mixture is still far from homogeneous after 30 revolutions. As shown in FIG. 10, nearly complete homogeneity is achieved after 240 revolutions.

In summary, it must be concluded that samples obtained using conventional thief probes are likely to contain significant errors. The insertion of a thief probe into a mixture causes extensive disturbances of the mixture structure, dragging particles along the path of insertion of the thief. The sample that is finally collected is likely to contain particles from all positions along the path. Even in the best case, samples were contaminated by particles originally located as far as 5 to 10 cm away from the sampling location causing errors of 10% or more, i.e., considerably larger than desirable for an accurate characterization of mixture structure.

The device of the present invention enables the extraction of an undisrupted column of powder from a vessel. The column of powder may then be sectioned into subunits using a specially designed discharge device. This allows one to render a large number of representative samples from a powder bed. The core sampler is able to resolve the interfacial layer with an axial resolution of less than 1 centimeter. The radial resolution is demonstrated to be equal to the diameter of the core. Therefore, the described sampling technique is a significantly more accurate means to extract undisturbed powder samples from an intended location. Additionally, the technique is more efficient and may be used to render a larger number of samples with less labor. Also, the weight of the collected samples is controllable. Given these advantages over conventional powder samplers and thieves, the sampling device described here is a simpler and better technique for determining content uniformity of powder within a vessel.

Having thus described the invention in detail, it is to be understood that the foregoing description is not intended to limit the spirit and scope thereof. What is desired to be protected by Letters Patent is set forth in the appended claims.

What is claimed is:

1. A powder sampling apparatus comprising:
   a cylindrical tube having an outer surface and an inner surface, an upper edge and a lower edge;
   an angle at the lower edge formed by the outer surface angled towards the inner surface to form a pointed circular lower edge of the cylinder; and
   a conical plow movable along the exterior of the cylindrical tube and a disk positionable on the base of the conical plow and rotatable with respect to the conical plow to cover the lower edge of the cylindrical tube.

2. The apparatus of claim 1 wherein the conical plow is interconnected with a rod, and the disk is interconnected with a sleeve positioned about the rod, the rod and sleeve attached to the cylindrical tube, the disk rotatable from a first position sitting on the plow to a second position covering the lower edge of the cylindrical tube.

3. The apparatus of claim 2 further comprising a rod handle interconnected with the rod for driving the plow, and a disk handle interconnected with the sleeve for rotating the disk.

4. The apparatus of claim 3, wherein the disk handle is rotatable with relation to the rod handle to move the disk.

5. The apparatus of claim 2, further comprising a plurality of eyelets for retaining the rod and sleeve along the cylindrical tube.

6. The apparatus of claim 5, wherein the rod and the sleeve are attached to extend parallel to the cylindrical tube.

7. The apparatus of claim 2, wherein the rod and the sleeve are rotatable with respect to each other.

8. The apparatus of claim 2, wherein the disk is positioned at a wide end of the conical plow.

9. A powder sampling apparatus comprising:
   a cylindrical tube having an outer surface and an inner surface, an upper edge and a lower edge;
   an angle at the lower edge formed by the outer surface angled towards the inner surface to form a point about the lower edge of the cylinder; and
   a conical plow interconnected with a rod, and a disk interconnected with a sleeve positioned about the rod, the rod and sleeve attached to the cylindrical tube, the disk rotatable from a first position sitting on the plow to a second position covering the lower edge of the cylindrical tube.

10. The apparatus of claim 9 further comprising a rod handle interconnected with the rod for driving the plow, and a disk handle interconnected with the sleeve for rotating the disk.

11. The apparatus of claim 10, wherein the disk handle is rotatable with relation to the rod handle to move the disk.

12. The apparatus of claim 9, further comprising a plurality of eyelets for retaining the rod and sleeve along the cylindrical tube.

13. The apparatus of claim 12, wherein the rod and the sleeve are attached to extend parallel to the cylindrical tube.

14. The apparatus of claim 9, wherein the rod and the sleeve are rotatable with respect to each other.

15. The apparatus of claim 9, wherein the disk is positioned at a wide end of the conical plow.

* * * * *